United States Patent [19]

Richter

[11] Patent Number: 4,631,031

[45] Date of Patent: Dec. 23, 1986

[54] ARTIFICIAL DENTAL PROSTHESIS

[76] Inventor: Ernst-Jürgen Richter, Neupforte 15, 5100 Aachen, Fed. Rep. of Germany

[21] Appl. No.: 722,262

[22] Filed: Apr. 11, 1985

[30] Foreign Application Priority Data

Apr. 12, 1984 [DE] Fed. Rep. of Germany ....... 3413811

[51] Int. Cl.$^4$ ............................................... A61C 8/00
[52] U.S. Cl. .................................................... 433/173
[58] Field of Search ................ 433/173, 174, 175, 176

[56] References Cited

U.S. PATENT DOCUMENTS

| | | | |
|---|---|---|---|
| 4,447,210 | 5/1984 | Hidaka et al. | 433/173 |
| 4,552,532 | 11/1985 | Mozsary | 433/174 |

FOREIGN PATENT DOCUMENTS

| | | |
|---|---|---|
| 1912120 | 12/1964 | Fed. Rep. of Germany . |
| 2534593 | 2/1975 | Fed. Rep. of Germany . |
| 2413883 | 9/1975 | Fed. Rep. of Germany . |
| 2755751 | 6/1978 | Fed. Rep. of Germany ...... 433/173 |
| 2950219 | 6/1980 | Fed. Rep. of Germany . |
| 3406448 | 8/1984 | Fed. Rep. of Germany . |
| 1123869 | 10/1956 | France . |
| 2282848 | 4/1976 | France ................. 433/173 |

Primary Examiner—Robert Peshock
Attorney, Agent, or Firm—Karl F. Ross; Herbert Dubno

[57] ABSTRACT

A two-stage elastic cushion is provided between a crown connecting member and an implant connecting member for a dental prosthesis in which the implant is adapted to be anchored in bone of the jaw of a patient. The yieldability during the first stage with increasing force is greater than in the second stage and is achieved by the selection of the material of elastic cushion for shaped factors.

13 Claims, 11 Drawing Figures

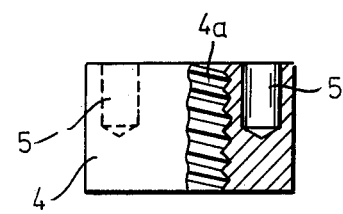
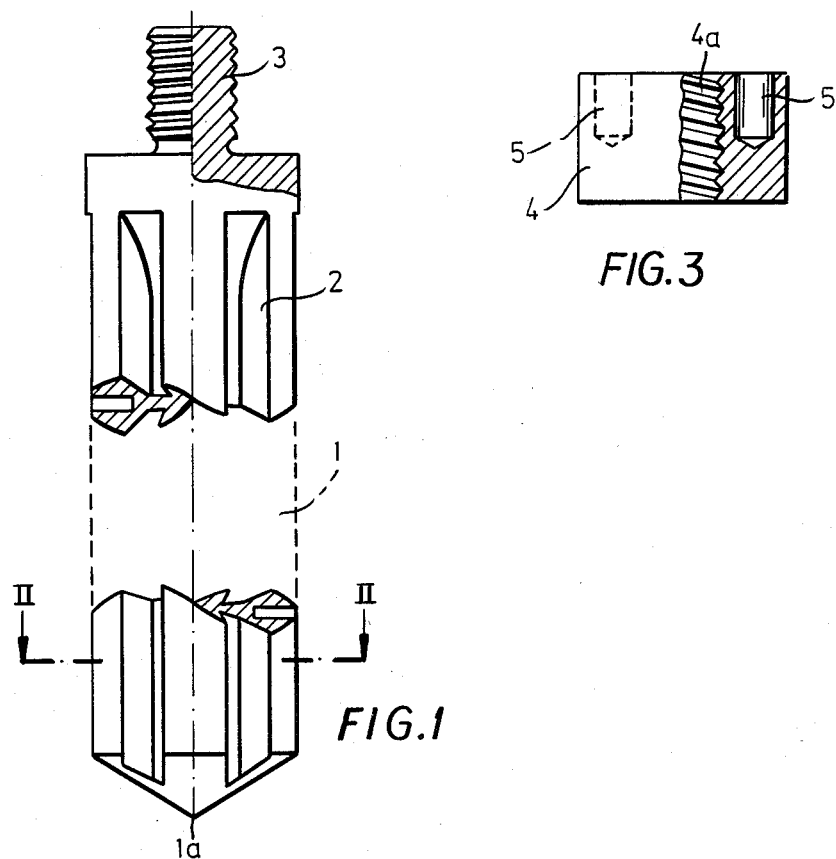
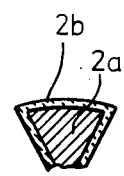
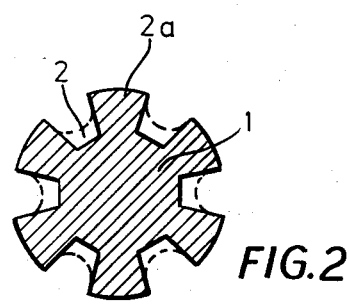
FIG.1
FIG.3
FIG.2
FIG.2A

ARTIFICIAL DENTAL PROSTHESIS

FIELD OF THE INVENTION

My present invention relates to a dental prosthesis and, more particularly, a prosthetic implant adapted to be set into the bone of a patient in the jaw region as a substitute to a natural-tooth anchored crown, bridge or the like.

BACKGROUND OF THE INVENTION

Over the last number of years animal and clinical experiments have shown the practicality of providing synthetic or artificial tooth roots which can be anchored in the jawbone of a patient and which can serve as supports for dental prosthetics. Such implants have been found to restore the bite and chewing quality in general and to improve the peridontal tissue in the remaining teeth of the patient by contrast with removable prostheses or plates which encounter all types of problems including tissue deterioration, poor fit and irritation, etc.

The loss of permanent side teeth tends to produce gaps which are detrimental to the patient because of the tendency of the remaining teeth to move in the direction of such gaps.

It has been proposed to fill such gaps with bridges attached to remaining teeth, but this procedure has problems as well, not only because of the undue stress which is applied to the support teeth but because the yieldability of the mesial support teeth results in a high degree of mobility of the bridge structure.

Disadvantages of such systems can be avoided at least in part by synthetic root implants which do not possess this kind of mobility and which are able to withstand the stresses which may be applied to a bridge supported on such implants. Nevertheless a certain degree of mobility or cushioning effect is desired for a number of resons. For example, the chewing characteristics are not as desirable if a prosthetic tooth is less moble than adjacent or proximal remaining teeth. The dental prosthesis should have the same mobility, within limits, as normal teeth if peridontal tissue damage is to be avoided.

Furthermore, some degree of cushioning is required to prevent overloading or overstressing of the prosthesis.

Consequently, it is desirable to have a certain degree of cushioning between the prosthetic tooth or the dental prosthesis and the implant or synthetic root. If an elastic cushion is provided to allow deformation and storage of the potential energy resulting from the kinetic energy of chewing, some of the problems outlined above can be solved.

However, in the past the provision of an elastic cushion has given rise to problems in anchoring the implant and in ensuring a uniform stressing of the peri-implant region.

It is known to provide an implant system using an elastic cushion and in which the implanted body adapted to be received in the jaw also receives, in turn, a so-called intramobile element in the form of an elastic cushion which is screwed into the implanted element or synthetic root.

The intramobile element essentially has the configuration of a cylindrical sleeve and is surrounded by a spacer sleeve which on the one hand is braced against the implanted element and on the other hand against the underside of a flange at the upper end of the intramobile element.

In a center screwthread of this cushion element, a so-called implantate post is screwed which constitutes the connecting member for the crown. The latter having a threaded pin, screw or bolt which can be screwed into an internal thread of the post. In this system, the intramobile element is stressed in compression by vertical stress in the flange region and in shear in the screwthread region. The result is a combined stress which is practically unpredictable or is poorly definable with mathematical-technical models.

The form of the intramobile element and the use of a homogeneous synthetic resin generally ensures that, at least with elastic deformation, this element undergoes deformation with a practically linear Hooke's law characteristic.

The threading of the intramobile element in the implant and of the crown connecting piece in the cushion is effected by hand so that fixed torques cannot be ensured.

Tests of these implant systems have shown that horizontal loading of the prosthesis, the horizontal yieldability is between 10 and 4 times less than the natural horizontal yieldability of molars. These tests have also shown that the elastic cushion which is about one hundred times too small by comparison with the internal mobility of molars.

The conclusion which is, therefore, inescapable is that the elasticity of the prosthesis with the intramobile element does not truly approximate that of natural teeth.

OBJECTS OF THE INVENTION

It is the principal object of the present invention, therefore, to provide a dental prosthesis of the implant type, i.e. adapted to be implanted in the bone, which avoids the drawbacks of earlier prostheses of this type.

Another object of this invention is to provide a dental prosthesis which more closely resembles as to its yieldability in all directions, the characteristics of natural teeth.

Yet another object of my invention is to provide a dental prosthesis having a cushion element whose wear as a result of the chewing function is more readily controlled and which can be easily replaced.

Still another object of the invention is to provide a compact dental prosthesis which is composed of a minimum number of parts and which is easily and simply fabricated, mounted and repaired or replaced when necessary.

SUMMARY OF THE INVENTION

These objects and others which will become apparent hereinafter are contained in accordance with the present invention in a dental prosthesis which includes an implant adapted to be anchored in the bone of the jaw, at least one prosthetic tooth mounted on this implant and a cushion element disposed between the tooth member and the implant and having an elasticity such that with increasing loading a two-stage deformation of the cushion element occurs such that in the first stage the yieldability is greater than the second stage.

The elastic cushion element according to the invention thus provides a joint between the practically immovable implant and the mobile tooth member which allows absorption not only of vertical but also of the horizontal stresses and thus provides a mobility which corresponds efficiently to the natural tooth mobility.

According to the invention the tooth mobility principle is characterized by a sharply bent force/displacement characteristic.

To limit the possibility of overloading with respect to the configuration of the elastic ring, the upper limit of the characteristic is determined by the natural mobility of a molar. The yieldability of the molar is a function of the structural substances of the tooth, the bond between the tooth and the bone structure, and since the characteristics of the prosthesis of the invention corresponds to the natural characteristic, it may be necessary to modify the elastic characteristic of the part implanted, bone or zone in an appropriate manner by the connection of the implant to the bone.

The loading of the implant is greater when the member connected to implant is not a single tooth, but rather when the implant element serves as a bridge post. To a close approximation the force upon the bridge member increases with the number of tooth elements n of the bridge member by the factor n/2 i.e. for the same slopes of the characteristics, the elastic cusion element must have an increased hardness.

The physiological loading resulting from chewing has a dynamic effect on the prosthesis although the characteristic describes the yieldability only in static loading. In natural teeth, these chewing stresses result primarily in a deeper depression of the teeth, something which is permitted by the elastic cushion element of the invention.

Lateral movements of the lower jaw apply horizontal forces at the respective contact points (articulation contacts) between the molars and generating gnashing formation which promote peridontal problems with respect to the tissues of the teeth. These horizontal movements can give rise to natural abrasion of the prosthesis, to the development of defects and also generate problems as to bridges carried by the implant.

The proper occlusion requires that the elastic ring provide a sufficient horizontal mobility under these conditions.

Advantageously, the implant is provided with a connecting member which is formed along its upper surface with an annular groove in which the cushion element of elastic material i.e. the elastic ring, is received.

Advantageously, a registering groove is provided in the underside of the crown connecting member so that the elastic ring is in part received in each of these two grooves. The upper connecting member or the crown connector can be resealably interconnected so that this assembly provides a simply adjusted and individually adjustable two-stage deformation of the ring.

The coupling member attached to the implant can have a conically upwardly widening central portion on whose lower end a cylindrical ceramic coated or sheathed shank is provided and on whose upper side carries a barrel-shaped boss or head whose outer surface defines a spherical segment and which can be separated outwardly to engage in a downwardly converging frustoconical recess of the crown connector or upper connecting member.

The internal groove on the upper face of the connecting member has a triangular cross-section whereas the groove on the lower face or underside of the upper connecting member can likewise have a triangular configuration.

The cylindrical shank can have an internal thread into which a threaded stud from the upper end of the implant can be screwed so that the connecting members and the cosmetic structure forming the exposed portion of the prosthesis can be removed and replaced as a unit.

The head is formed with two longitudinal extending slits which divide this head into a plurality of free standing members adapted to be urged outwardly against the wall of the frustoconical recess by a wedging screw having a conical head.

The wedging action draws the upper connecting member toward the lower connecting member to provide the desired degree of precompression of the elastic ring and resistance to movement of the upper member with respect to the lower member. An outwardly open groove forms a neck between the head and the remainder of the lower connecting member so as to increase the deflectability of the head segments.

The two-stage deformability of the elastic cushion element or ring with increasing loading in accordance with the sharply bent force-displacement characteristic parts to the synthetic teeth structure, a characteristic closely approximating that of the natural tooth.

The two-stage deformation in which the two limbs of the characteristics have different slopes joined at an angle can be generated by forming an elastic ring from two materials having different moduli $\epsilon$ of elasticity.

It is also possible to so confine the ring in the annular grooves that the portion subject to compression changes at the slope change of the characteristic. The yieldability can be varied by selecting the material constituting the elastic ring i.e. its elasticity modulus. In addition the elastic ring can be provided with a prestress.

The crown connector (upper connecting member) is provided in the region of its upper half with an internal screw thread into which the threaded stud or shank of a crown can be screwed. By tightening this screw, the crown can be affixed to the crown connector in an assembled manner.

The periphery of the crown connector can widen downwardly and outwardly while the interior of the crown can be oppositely tapered so that a surface contact is ensured between the crown and the crown connector. The angle made by the frustoconical flank with the vertical can be about 5°, a value which promotes frictional contact between the crown and the crown connector, the frictional contact being further promoted by the screwthread connection between the two.

The crown connector is fully received or enveloped within the crown so that a practically closed body is formed thereby.

The crown connector is provided in the region to its lower half with the aforementioned downwardly frustoconical convergent recess in which the head of the implant connector (lower connecting member) is engaged.

The annular groove formed in the underside of the crown connector can have the same cross-section as the annular groove formed on the upper surface of the implant connector.

The implant itself is provided along its outer periphery with longitudinal extending ribs alternating with longitudinal extending outwardly open grooves and can also have a ceramic-coating which ensures a particularly effective anchorage in a jawbone.

Onto the threaded stud on the upper end of the implant, a threaded nut can be securely fastened to the implant to cover the latter and which is applied to the implant to enable it to be seated in the jaw and grow into place.

One or more axial bores preferably a pair of such bores located diametrically opposite to one another, can be provided for engagement by pins of a tool or key for removal of the nut whereby the lower connector, elastic ring, crown connector and crown can then be applied.

BRIEF DESCRIPTION OF THE DRAWING

The above and other objects, features and advantages of the present invention will become more readily apparent from the following description, reference being made to the accompanying drawing in which:

FIG. 1 is a partial broken away elevational view of an implant for setting in a jawbone in accordance with the invention, greatly enlarged as to scale as are all of the FIGURES subsequently described;

FIG. 2 is a section taken along the line II—II of FIG. 1;

FIG. 2a is a detail of a section corresponding to FIG. 2 according to another embodiment of the invention;

FIG. 3 is a partial section through the nut which can be applied to the stud of FIG. 1;

SPECIFIC DESCRIPTION

Figure 7:
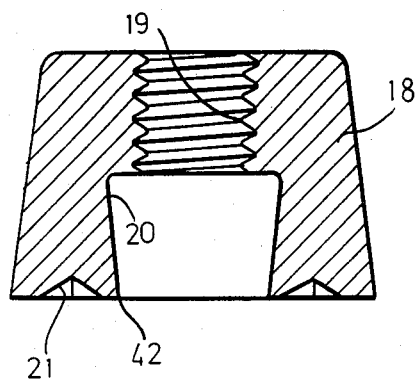
FIG. 7 is an axial section through the upper connecting member or crown connector.

The implant 1 shown in FIG. 1 comprises a shank formed with axial extending grooves 2 separated by ribs 2a, one of which can be seen in FIG. 2a to have a coating or sheath 2b of a ceramic, it being understood that the entire implant can be so coated.

The implant 1 has a point 1a enabling it to be driven into a slightly smaller hole previously drilled in the bone, the driving action being facilitated by the application of a nut 4 to a thread stud 3 at the upper end of the implant. The nut 4 is cylindrical and of the same diameter as the implant to permit the implant to be driven into the bone without damage to the stud. A pair of axial bores 5 diametrically opposite one another can receive pins of a tool allowing the nut to be unthreaded from the stud.

The ceramic coating 2b ensures anchorage in the bone. The grooves 2 are formed symmetrically on the implant.

The nut 4 has an internal screwthread 4a receiving the stud 3.

Figure 4:
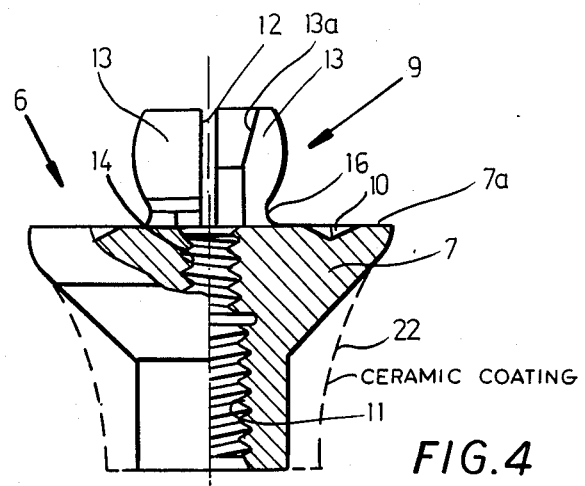
FIG. 4 is an elevational view partial in axial section of the lower coupling member.

From FIG. 4 it will be apparent that a lower connecting member or implant connector 6 can have the cylindrical lower shank 8 with an internal screwthread 11 adapted to be screwed onto the stud 3. Above the shank 8 a frustoconical widening portion or middle part 7 is provided which defines an upwardly facing surface 7a.

The barrel-shaped head 9 extends axially upwardly from the center of the middle part 7.

On the upper surface 7a of the middle part 7, an annular groove 10 is provided and has a triangular cross section.

The head 9 is provided with at least two longitudinal slits 12 which lie diametrically opposite one another and separate the head into a plurality of deflectable segments 13. The head 9 is hollow and its interior communicates with an internally threaded bore 14 in the middle part 7.

Figure 5:
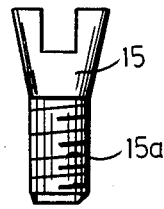
FIG. 5 is an elevational view of the wedge screw.

A wedging screw (FIG. 5) has a threaded shank 15a which can be screwed into the threaded bore 14 and a frustoconical head 15 which is complementary to the frustoconical recess 13a of this head so that with progressive advance of the screw the sectors 13 are wedged outwardly and apart.

At the junctions of these sectors 13 in the middle part 7, an outwardly open groove 16 is provided to reduce the wall thickness in this region and facilitate the outward deflection of the sections and thereby increase the yieldability thereof.

Figure 6:
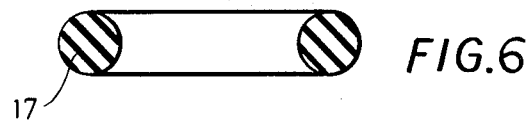
FIG. 6 is an axial section of the elastic cushion element or ring.
Figure 9:
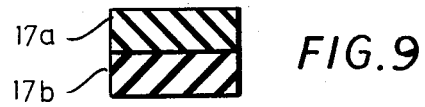
FIG. 9 is a detail of another of a ring cross section which can be used.

The elastic element has been shown in FIG. 6 and comprises a ring 17 which here is of circular cross section. In the embodiment of FIG. 9, the ring can have a rectangular cross-section and can be provided from two different materials 17a and 17b one of which is substantially more than the other. The grooves can have complementary rectangular cross section. Alternatively the elastic ring 17' in FIG. 11 is shaped with a central portion of greater volume and a pair of projecting lateral portions 17' so that only when these lateral portions are engaged is the resistance to compression increased.

Figure 10:
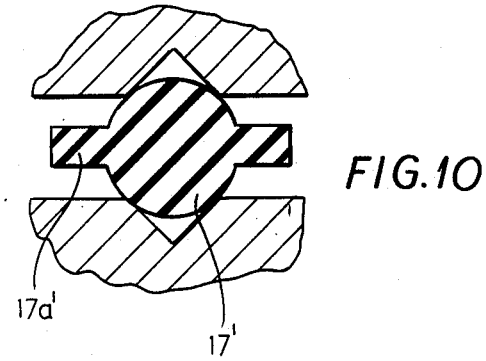
FIG. 10 is a cross sectional view showing a portion of another ring and the grooves in which it is received.

FIGS. 6, 9 and 10 make clear that the cushion 17 is subject to a two-stage elastic deformability with the first stage compression being more yieldable than that of the second stage.

Figure 8:
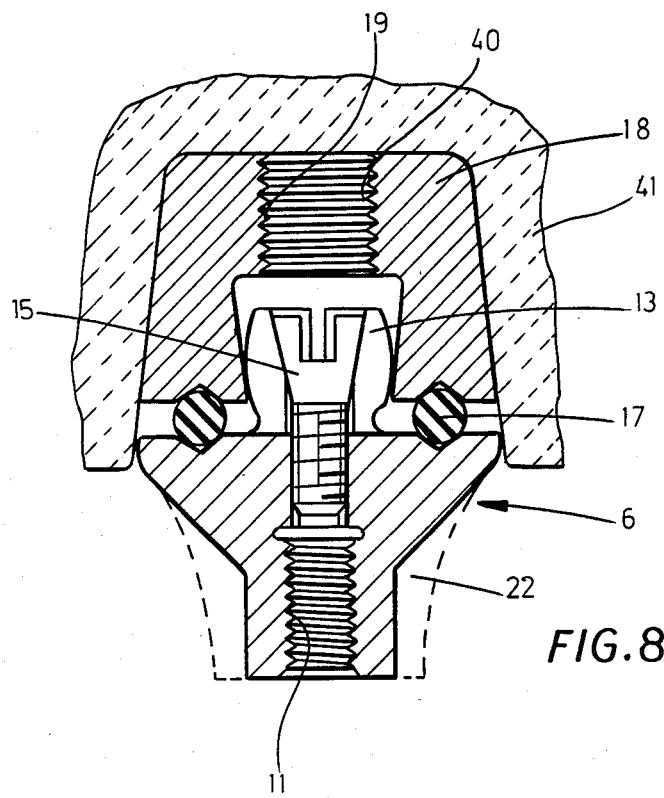
FIG. 8 is a partial section illustrating the parts of FIGS. 4 through 7 assembled together.

The crown connector shown at 18 in FIG. 7 is formed at its upper half with an internal screwthread 19 into which the threaded stud 40 of a crown 41 can be screwed (see FIG. 8). The lower half of the crown connector 18 has an upwardly widening or downwardly narrowing frustoconical recess 20 whose mouth 42 is dimensioned to receive the head 9 before the sectors 13 are spread.

The underside of the connector 18 is provided with a further groove 21 which is also of triangular cross section and registers with the groove 10 so that both of these grooves can receive the elastic ring 17.

The periphery of the crown connector frustoconically widens downwardly while the crown 41 is of a complementary configuration to ensure a snug connection between the two.

After the implant 1 has been set in place and the nut 4 applied, healing is permitted to permit tissue growth around the implant and bone fusion therewith. When healing is completed the nut 4 is removed and the stud 3 exposed. The connecting member 6 is then threaded onto the stud 3 and thus anchors the assembly 18, 17, 15 in place, the screw 15, 15a holding this assembly together. The screw 15 can then be tightened to generate the desired freedom between the head 9 and the upper member 18 and the requisite member stress on the ring 17.

Because the head 9 has a ball-shaped periphery, the horizontal loading member 18 rolls somewhat on the ball surface and the ring 17 is reproducibly compressed.

The member stress can be controlled by a torque driver acting on the screw 15, 15a. The crown can then be applied and of course will be prepared to match any remaining teeth in the mouth of the patient.

The structure described has a multi-functional effect in that the elastic ring 17 acts as a joint allowing horizontal and vertical controlled embodiment as well as a seal. The ball-shaped head acts not only to center the connecting members with respect to one another but to arrest the removable member 18 and provide vertical adjustment and prestress.

The coupling member 6 and 18 and the screw 15 are composed of noble metal alloys or corrosive free alloys while rubber or synthetic resin is used for the elastic ring.

With vertical loading on the prosthesis the elastic element 17 is compressed so that its previously tangential contact with the inclined flanks of the grooves 10 and 21 is transformed into the surface contact. With increasing compaction, however, the ring 17 is confined by the grooves so that additional force is necessary for a given further displacement.

High yieldability then becomes low yieldability at the break in the characteristic.

With horizontal force only partial segments of the elastic ring are compressed, these being more readily deformable than the entire cushion element. Consequently there is a greater yieldability for lateral loading.

With appropriate variation in the materials and especially in their moduli of elasticity, the slope or configuration of the force-displacing characteristic can be changed. By altering the prestress of the element 17, for example, by the screw 15, the first stage yieldability can be altered.

As can be seen from FIG. 4 as well, the implant connector 6 can be coated externally over its shank 8 and the frustoconical portion of the middle part 7 by a bone-compatible ceramic sheath 22.

I claim:

1. A crown attachment comprising:
   an implant adapted to be seated in a bone of a jaw and having an attachment end turned away from said bone and having an axis;
   a first coupling member fixed to said end of said implant and provided with an annular first formation located along said axis and surrounded by an annular shoulder lying in a plane generally perpendicular to said axis;
   a second coupling member formed centrally with a second formation matingly engageable with said first formation with freedom of swivelling and axial mobility therebetween, and with an annular shoulder surrounding said second formation and lying in a plane and juxtaposed with said shoulder of said first coupling member, said shoulders being each formed with a respective groove opening toward the other shoulder and registering with one another;
   a dental crown affixed to said second coupling member; and
   an elastic ring disposed in said grooves and of a material and so associated with the shapes of said grooves as to yieldably resist displacement of said shoulders toward one another with a force/displacement characteristic having a break between an initial section of greater yieldability and an adjacent subsequent section of lesser yieldability.

2. The crown attachment defined in claim 1 wherein said first coupling member is provided with a portion, frustoconically widening toward said second coupling member and terminating at its side opposite said second coupling member in a cylindrical boss, said first formation being a barrel-shaped head.

3. The crown attachment defined in claim 2 wherein said boss is formed with an internal screw thread threadedly receiving said end of said implant.

4. The crown attachment defined in claim 2 wherein said head is subdivided by at least two slits into a plurality of outwardly deflectable sectors each attached at only one end of said frustoconical portion.

5. The crown attachment defined in claim 4 wherein said first coupling member has a pair of flanks converging toward one another away from said second coupling member.

6. The crown attachment defined in claim 4 wherein said barrel-shaped head is separated from said annular shoulder of said first coupling member by a neck undercutting said head.

7. The crown attachment defined in claim 4 wherein said elastic ring has a circular cross section.

8. The crown attachment defined in claim 4 wherein said elastic ring has a rectangular cross section.

9. The crown attachment defined in claim 4, further comprising a frustoconical head screw threadedly received in said first coupling member for adjusting the relative mobility of said first and second coupling members and a prestress on said elastic ring.

10. The crown attachment defined in claim 4 wherein said frustoconical portion is provided with an internal thread receiving a screw traversing said crown and said second coupling member.

11. The crown attachment defined in claim 4 wherein said second formation is a frustoconical cavity in said second member converging toward said first coupling member and receiving said head.

12. The crown attachment defined in claim 11 wherein said second coupling member has flanks converging toward one another away from said first coupling member.

13. The crown attachment defined in claim 11 wherein said second coupling member is of frustoconical outer configuration enlarging toward said first coupling member.

* * * * *